(12) United States Patent
Onishi et al.

(10) Patent No.: US 7,173,141 B2
(45) Date of Patent: Feb. 6, 2007

(54) CHIRAL LACTONES

(75) Inventors: Tomoyuki Onishi, Kawasaki (JP); Robert M. Williams, Fort Collins, CO (US)

(73) Assignees: Colorado State University Research Foundation, Fort Collins, CO (US); Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/119,905

(22) Filed: May 3, 2005

(65) Prior Publication Data

US 2006/0205816 A1    Sep. 14, 2006

Related U.S. Application Data

(60) Provisional application No. 60/659,415, filed on Mar. 9, 2005.

(51) Int. Cl.
*C07D 319/00* (2006.01)
*C07D 323/04* (2006.01)
*C07D 407/00* (2006.01)
*C07D 59/00* (2006.01)
*C07D 62/00* (2006.01)

(52) U.S. Cl. .................. 549/274; 562/465; 562/579

(58) Field of Classification Search ............. 549/274; 562/465, 579
See application file for complete search history.

(56) References Cited

OTHER PUBLICATIONS

Andrus et al., Organic Letters, "Anti-selective glycolate aldol additions with an oxapyrone boron enolate", vol. 2, pp. 3035-3037.*

P. Sinclair, et al., "Electrophilic Glycinates: New and Versatile Templates for Asymmetric Amino Acid Synthesis", J. Am. Chem. Soc., 1986, 108, pp. 1103-1104.

Y. Aoyagi, et al., "Asymmetric Synthesis of [2,3-$^{13}C_2$,$^{15}N$]-4-Benzyloxy-5,6-diphenyl-2,3,5,6-tetrahydro-4H-oxazine-2-one via Lipase TL-Mediated Kinetic Resolution of Benzoin: General Procedure for the Synthesis of [2,3-$^{13}C_2$,$^{15}N$]-L-Alanine", J. Org. Chem., 2001, 66, pp. 8010-8014.

M. Andrus, et al., "Anti-Selective Glycolate Aldol Additions with an Oxapyrone Boron Enolate", Organic Letters, 2000, vol. 2, No. 19, pp. 3035-3037.

M. Andrus, et al., "Synthesis of the Left-Hand Portion of Geldanamycin Using an Anti Glycolate Aldol Reaction", Organic Letters, 2001, vol. 3, No. 2, pp. 259-262.

M. Andrus, et al., "Total Synthesis of (+)-Geldanamycin and (−)-o-Quinogeldanamycin with Use of Asymmetric Anti- and Syn-Glycolate Aldol Reactions", Organic Letters, 2002, vol. 4, No. 20, pp. 3549-3552.

Y. Matsumura, et al., "Copper Ion-Induced Activation and Asymmetric Benzoylation of 1,2-Diols: Kinetic Chiral Molecular Recognition",J. Am. Chem. Soc., 2003, 125, pp. 2052-2053.

* cited by examiner

*Primary Examiner*—Thomas McKenzie
*Assistant Examiner*—Niloofar Rahmani
(74) *Attorney, Agent, or Firm*—Oblon, Spivak, McClelland, Maier & Neustadt, P.C.

(57) ABSTRACT

Lactones represented by the formula 2a or 2b:

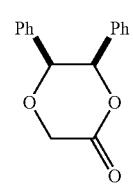

2a

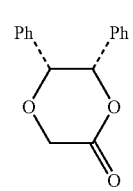

2b are provided, where each Ph is, independently, an unsubstituted or substituted phenyl group. These lactones are suitable for the synthesis of various α-hydroxy acids and 1,2-diols.

20 Claims, 2 Drawing Sheets

1a          1b

R = Cbz or Boc 2a　　　　　2b　　　　　3a　　　　　3b

CHIRAL LACTONES

CONTINUING APPLICATION INFORMATION

This application claims priority to U.S. provisional application Ser. No. 60/659,415, filed on Mar. 9, 2005, and incorporated herein by reference.

BACKGROUND OF THE INVENTION

1. Field of the Invention

The present invention relates to chiral lactones, methods of making the lactones and methods of use thereof.

2. Description of the Background

In our own work (ref. 1), we have extensively demonstrated that (5S,6R)- and (5R,6S)-4-Cbz and t-Boc-5,6-diphenyl-2,3,5,6-tetrahydro-4H-1,4-oxazin 2-ones (1a and 1b, FIG. 1) are useful as chiral, nonracemic glycine templates for the synthesis of structurally diverse α-amino acids. The compounds (2a and 2b, FIG. 2), in which Cbz- or t-Boc-protected NH is substituted for an oxygen atom, would be useful to synthesize various chiral α-hydroxy acids, however, no synthesis has been reported so far. Though there are papers which describes glycolate Aldol reaction of trans-diphenyl lactones (3a and 3b) (see ref. 2), diastereoselectivity is not necessarily high and no other application such as alkylation has been reported. Thus, there remains a need for a synthetic procedure to obtain novel lactones as chiral building blocks for the synthesis of various α-hydroxy acids and 1,2-diols.

SUMMARY OF THE INVENTION

It is an object of the present invention to provide novel lactones as chiral building blocks for the synthesis of various α-hydroxy acids and 1,2-diols.

It is another object of the present invention to provide methods of synthesizing the novel lactone.

It is another object of the present invention to provide a method of synthesizing substituted α-hydroxy acids using the lactone as a starting material.

The objects of the present invention, and others, may be accomplished with a lactone represented by the formula 2a or 2b:

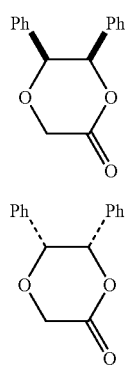

where each Ph is, independently, an unsubstituted or substituted phenyl group.

The objects of the present invention may also be accomplished with a method of synthesizing the lactone described above, comprising reacting a hydroxy ester of the formula:

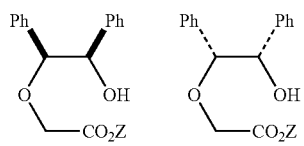

with an acid, wherein Z is an alkyl group.

The objects of the present invention may also be accomplished with a method of synthesizing a substituted α-hydroxy acid represented by the formula:

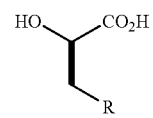

where R is a substituted alkyl group, an unsubstituted alkyl group, a substituted aryl group, an unsubstituted aryl group, a substituted alkoxycarbonyl group or an unsubstituted alkoxycarbonyl group, comprising treating the lactone described above with a base and a compound represented by the formula X—CH$_2$—R to produce a compound represented by the formula (12):

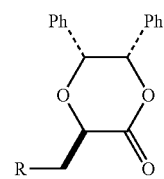

where X is a leaving group, followed by catalytic hydrogenating the compound represented by the formula (12).

A more complete appreciation of the invention and many of the attendant advantages thereof will be readily obtained as the same becomes better understood by reference to the following Figures in conjunction with the detailed description below.

DETAILED DESCRIPTION OF THE INVENTION

Figure 1:
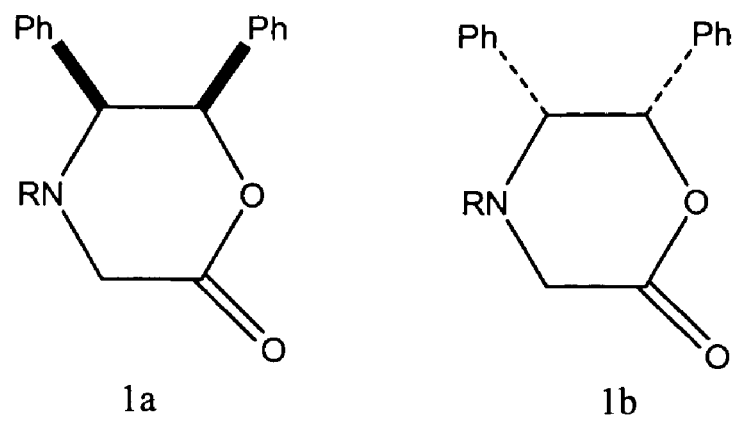
FIG. 1: Glycine templates for the synthesis of α-amino acids.
Figure 2:
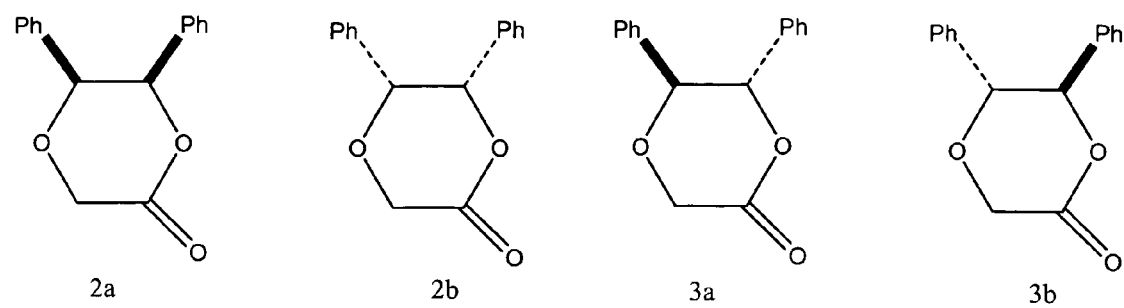
FIG. 2: Novel lactones (2a and 2b) for the synthesis of α-hydroxy acids and 1,2-diols.

The present invention provides a chiral lactone represented by the formula 2a or 2b:

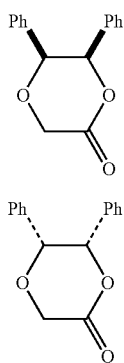

The Ph groups may be, independently, an unsubstituted phenyl group or a substituted phenyl group. Suitable substituents for the phenyl group include an alkoxy group (preferably having 1 to 7 carbon atoms), a nitro group, an alkyl group (preferably having 1 to 6 carbon atoms) and a halogen atom.

In a preferred embodiment, the lactone has an enantiomeric excess (e.e.) of at least 50% e.e. In more preferred embodiments, has an e.e. of at least 75% e.e., at least 90% e.e., 95% e.e or higher.

As discussed above, the present invention also provides a method of synthesizing the lactone by reacting a hydroxy ester of the formula:

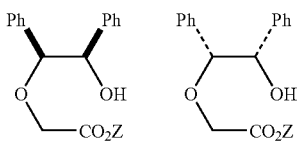

with an acid.

Suitable acids is hydrochloric acid, hydrobromic acid, hydroiodic acid, sulfuric acid, methanesulfonic acid, trifluoromethanesulfonic acid, benzenesulfonic acid, p-toluenesulfonic acid, trifluoroacetic acid or acidic ion exchange resin (ion exchange resin acid catalyst). In a preferred embodiment, the acid is trifluoroacetic acid.

As noted above, Z is an alkyl group. A preferred alkyl group is a t-butyl group.

For the synthesis of lactones 1a and 1b, erythro-2-amino-l1,2-diphenylethanol (ref. 1b) in optically pure form can be used as a starting material. On the other hand, meso-hydrobenzoin (4), the corresponding starting material for the synthesis of 2a and 2b, is a racemic compound and therefore it was necessary to use an asymmetric reaction for the preparation of 2a and 2b. Recently, Matsumura et al. reported a copper ion-induced activation and asymmetric benzoylation of 1,2-diols by Matsumura et al. (see ref. 3). We studied ways to prepare 2a and 2b using the asymmetric desymmetrization of meso-hydrobenzoin described.

According to that reference, the optical purity of the monobenzoylated compound 5S is 94% e.e. However, that is not high enough for our purpose. After exploration, we found that optical purity could be improved to >95% e.e. by performing the reaction at a low temperature such as −15° C. (Scheme 1). Next, 5S was reacted with tert-butyl bromoacetate in the presence of NaH to give 6X in 78% yield. The compound 6X was converted to lactone 2X in 53% yield over 2 steps via saponification followed by lactonization. However, it was realized that 2X was completely racemic. Racemization seemed to occur during the coupling reaction with tert-butyl bromoacetate via transesterification. See Scheme 1 below.

Scheme 1. Synthetic route to lactone 2a and 2b.

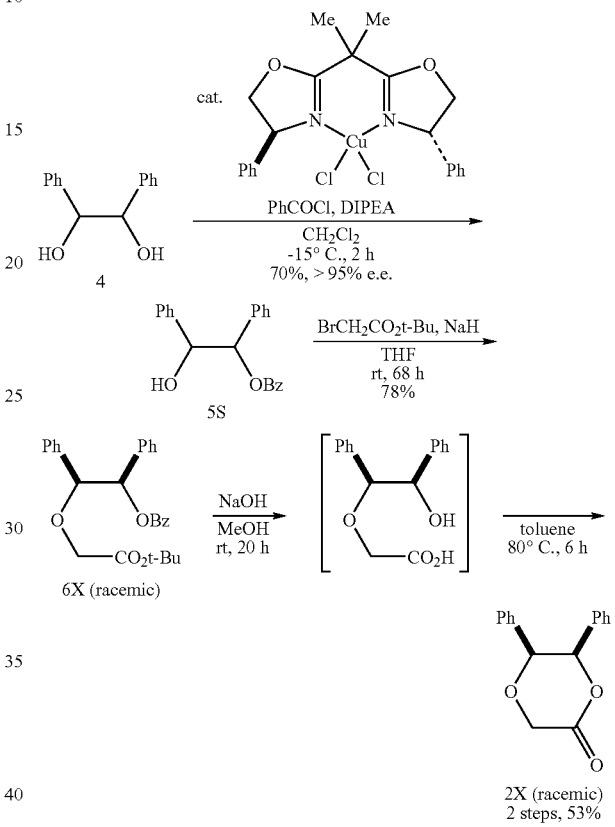

To avoid racemization, the benzoyl group should be substituted for another group such as the tetrahydropyranyl group. For this purpose, 5S was converted to THP ether 8S in 70% yield over 2 steps via THP ether formation followed by saponification (Scheme 2). Then, 8S was coupled with tert-butyl bromoacetate to give, 9S in 74% yield. After removal of the THP group by the treatment with p-TsOH in methanol, deprotection of the carboxyl group and lactonization were performed by the treatment with trifluoroacetic acid to give the desired product 2b in 57% yield over 2 steps. Enantiomer 2a was also prepared from (1R,2S)-2-hydroxy-1,2-diphenylethyl benzoate by a similar procedure. The enantiomeric purity of 2b was proved to be >95% e.e. by normal phase HPLC using a Chiralpak AS column.

Scheme 2. Revised synthetic route to lactone 2a and 2b

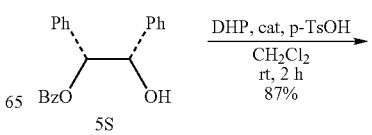

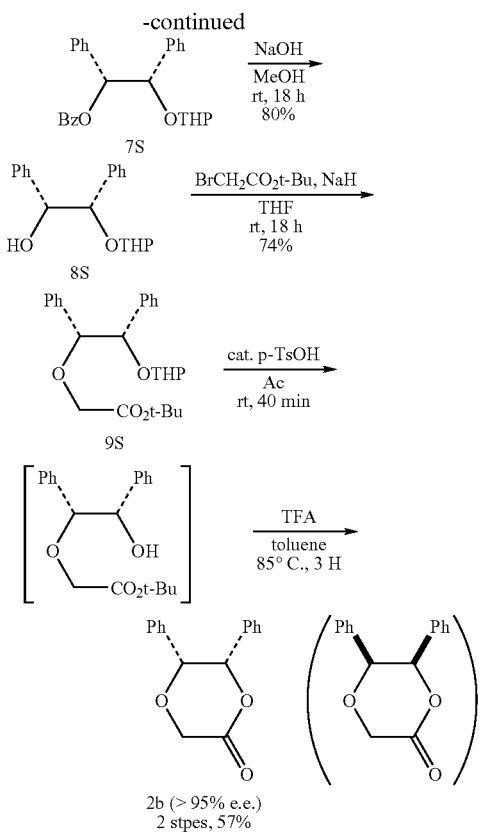

The present invention also provides a method of synthesizing a substituted α-hydroxy acid represented by the formula:

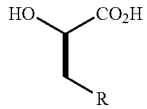

in which R is a substituted alkyl group, an unsubstituted alkyl group, a substituted aryl group, an unsubstituted aryl group, a substituted alkoxycarbonyl group or an unsubstituted alkoxycarbonyl group. Suitable substituents for the alkyl group, the aryl group and the alkoxycarbonyl group include an alkoxy group (preferably having 1 to 7 carbon atoms), a nitro group, an alkyl group (preferably having 1 to 6 carbon atoms) and a halogen atom. In a preferred embodiment, R is a tert-butoxycarbonyl group.

In this procedure, the lactone is treated a base and a compound represented by the formula X—CH$_2$—R to produce a compound represented by the formula (12):

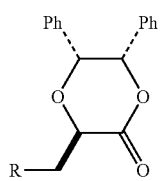

The nature of the base is not particularly limited in that it must be strong enough to deprotonate the lactone in order to facilitate reaction with the compound represented by the formula R—CH$_2$—X. Suitable bases include lithium hydride, sodium hydride, potassium hydride, potassium tert-butoxide, lithium bis (trimethylsilyl) amide, sodium bis (trimethylsilyl) amide, potassium bis (trimethylsilyl)amide or lithium diisopropylamide.

The group X is a leaving group. The nature of X is not particularly limited provided that R—CH$_2$—X reacts with the deprotonated lactone. Suitable examples of X include Cl, Br and I. In one embodiment, X is Br.

Next, compound (12) is subjected to catalytic hydrogenation. The nature of the conditions for catalytic hydrogenation are not particularly limited, and are well-known in the art. There is no particular limitation imposed on the catalysts to be used for reduction insofar as they allow the reaction to proceed smoothly. Examples thereof include palladium, palladium hydroxide and palladium (II) chloride and the like. These catalysts may be held on carbon or the like and may contain water. Among them, palladium hydroxide and palladium (II) chloride are preferred.

Thus, the strategy utilizing 2a and 2b as a chiral building blocks for the synthesis of α-hydroxy carboxylic acids is based on the use of catalytic hydrogenation to remove the chiral auxiliary. To demonstrate its utility, a synthesis of D-malic acid-β-tert-butyl ester (11) was examined (Scheme 3). First, 2b was treated with tert-butyl bromoacetate in the presence of sodium bis (trimethylsilyl) amide to give 10 in 54% yield. By $^1$H-NMR analysis of crude product, it was confirmed that the diastereoselectivity was better than 10:1. Using Pd (OH)$_2$ as a catalyst, 11 is cleanly produced from catalytic hydrogenation of 10.

Scheme 3. Synthesis of D-malic acid-β-tert-butyl ester (11)

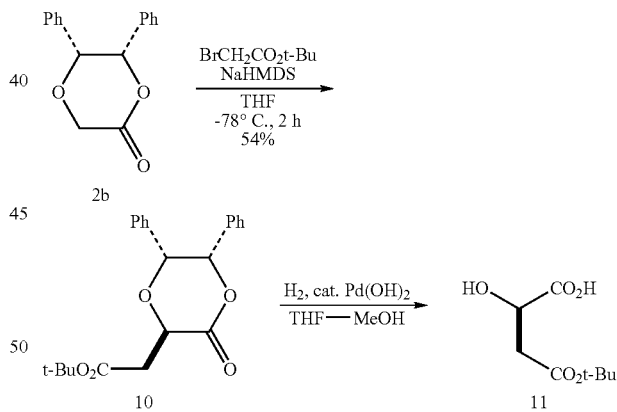

In conclusion, the novel lactones, which are potent chiral building blocks for the synthesis of α-hydroxy carboxylic acids, were prepared in optically pure form from meso-fiydrobenzoin over 6 steps. These lactones will be suitable for the synthesis of various (α-hydroxy acids and 1,2-diols.

EXAMPLES

Having generally described this invention, a further understanding can be obtained by reference to certain specific examples which are provided herein for purposes of illustration only and are not intended to be limiting unless otherwise specified.

(R)-(+)-2,2'-Isopropylidenebis (4-phenyl-2-oxazoline), (S)-(−) 2,2'-isopropylidenebis-(4-phenyl-2-oxazoline) and meso-hydrobenzoin, can be purchased from Aldrich. Chiralcel OJ-H and Chiralpak AS can be purchased from Daicel Chemical Industries, Ltd.

(1S,2R)-2-Hydroxy-1,2-diphenylethyl benzoate (5S)[3]

To a suspension of meso-hydrobenzoin (9.90 g, 46.2 mmol) and (S)-(−) 2,2'-isopropylidene-bis(4-phenyl 2-oxazoline)-CuCl$_2$ complex (1.0 g, 2.13 mmol) in dichloromethane (220 ml) was added diisopropylethylamine (14.8 ml, 85.2 mmol) at −15° C. After stirring for 2 min at −15° C., benzoyl chloride (4.95 ml, 42.6 mmol) was added. After stirring for 2 h at −15° C., a 1.5 M solution of hydrochloric acid (400 ml) and dichloromethane (300 ml) were added. After phase separation, the organic layer was washed with water (100 ml) twice and was dried over anhydrous sodium sulfate. After concentration, the residue was dissolved in ethanol (102.7 ml), ethyl acetate (29.3 ml) and water (14.7 ml) under reflux. The mixture was gradually cooled to rt, and the resultant white solid was collected and was washed with cold ethanol to give 5S (10.3 g, 70%, >95% e.e.). Enantiomer purity was determined by normal phase HPLC using a Chiralcel OJ-H column.[3]

(1S*,2R*)-2-tert-Butoxycarbonylmethoxy-1,2-diphenylethyl benzoate (6X)

To a suspension of sodium hydride (60% oil dispersion; 349 mg, 8.71 mmol) in dry tetrahydrofuran (21.8 ml) were added a solution of 5S (2.77 g, 8.71 mmol) and tert-butyl bromoacetate (1.55 ml, 10.5 mmol) in dry tetrahydrofuran (21.8 ml) at 0° C. After stirring for 68 h at rt, the reaction mixture was concentrated in vacuo. After addition of water, the product was extracted with ethyl acetate three times and the organic layer was dried over anhydrous sulfate. After concentration in vacuo, the residue was purified by silica gel chromatography (eluted with 6:1 hexane:AcOEt) to give 6X (2.94 g, 78%) as a white solid. $^1$H NMR (400 MHz, CDCl$_3$)δ CHCl$_3$: 1.38 (s, 9H), 3.77 (d, J=16.4 Hz ,1H), 3.94 (d, J=16.4 Hz, 1H), 4.91 (d, J=4.8 Hz, 1H), 6.28 (d, J=4.8 Hz, 1H), 7.17–7.29 (m, 10H), 7.36–7.42 (m, 2H), 7.48–7.53 (m, 1H), 7.98 (d,J=7.6 Hz, 2H); $^{13}$C NMR (100 MHz, CDCl$_3$) δ CHCl$_3$: 28.0, 66.8, 78.1, 81.4, 84.0, 127.6, 127.8, 127.9, 128.0, 128.2, 128.3, 128.4, 129.7, 130.2, 132.9, 136.5, 136.9, 165.3, 169.1; IR (NaCl/neat) 1747, 1725, 1452, 1368, 1315, 1271, 1229, 1162, 1127, 709 cm$^{-1}$; HRMS (FAB+) calcd for C$_{27}$H$_{29}$O$_5$ (m/z) 433.2015, found (m/z) 433.2006.

(5S*,6R*)-5,6-Diphenyl-[1,4]dioxan2-one (2X)

To 6X (2.94 g, 6.79 mmol) was added a solution of sodium hydroxide (326 mg, 8.15 mmol) in methanol (27.2 ml). After stirring for 20 h at rt, 37% hydrochloric acid (669 μl, 8.15 mmol) was added. After concentration in vacuo, a 0.4 M solution of hydrochloric acid (50 ml) was added. The resultant product (hydroxy carboxylic acid) was extracted with ethyl acetate four times and the organic layer was dried over anhydrous sodium sulfate. After concentration, the residue was dissolved in toluene (34 ml) followed by addition of trifluoroacetic acid (105 μl, 1.36 mmol). After stirring for 6 h at 80° C., the reaction mixture was concentrated in vacuo and the residue was purified by silica gel chromatography (eluted with 6:1 hexane:AcOEt) to give 2X (921 mg, 53%) as a white solid.

$[\alpha]^D_{25}$=0.0 (CHCl$_3$, c=1); $^1$H NMR (400 MHz, CDCl$_3$) δ CHCl$_3$: 4.64 (d, J=17.8 Hz, 1H), 4.82 (d, J=17.8 Hz, 1H), 5.22 (d, J=3.4 Hz, 1H), 5.60 (d, J=3.4 Hz, 1H), 6.83–6.87 (m, 2H), 6.92–6.96 (m, 2H), 7.13–7.24 (m, 6H); $^{13}$C NMR (100 MHz, CDCl$_3$) δ CHCl$_3$: 66.7, 77.2, 84.2, 126.2, 127.6, 127.8, 128.1, 128.3, 128.5, 133.8, 134.8, 166.7; IR (NaCl/neat) 1743, 1384, 1341, 1217, 1124, 1053, 1035, 1018, 733, 700 cm$^{-1}$; HRMS (FAB+) calcd for C$_{16}$H$_{15}$O$_3$ (m/z) 255.1021, found (m/z) 255.1028.

(1 R,2S)-1,2-Diphenyl2-(tetrahydropyran 2-yloxy)ethyl benzoate (7S)

To a solution of 5S (2.00 g, 6.28 mmol) and p-toluenesulfonic acid monohydrate (120 mg, 0.628 mmol) in dichloromethane (30.4 ml) was added 3,4-dihydro-2H-pyran (859 μl, 9.42 mmol). After stirring for 2 h at rt, a saturated aqueous solution of sodium bicarbonate (10 ml) was added. The product was extracted with dichloromethane twice and the organic layer was dried over anhydrous sodium sulfate. After concentration in vacuo, the residue was purified by silica gel chromatography (eluted with 8:1 hexane:AcOEt) to give 7S (2.21 g, 87%) as a white solid.

$[\alpha]^D_{25}$=+71.8 (CHCl$_3$, c=1); $^1$H NMR (major isomer: 400 MHz, CDCl$_3$) δ CHCl$_3$: 1.22–1.75 (m, 6H), 3.07–3.52 (m, 2H), 4.51 (t, J=2.4 Hz, 1H), 5.03 (d, J=6.6 Hz, 1H), 6.11 (d, J= 6.6 Hz, 1H), 7.15–7.52 (m, 13H), 7.90–7.98 (m, 2H); $^{13}$C NMR (major isomer: 100 MHz, CDCl$_3$) δ CHCl$_3$: 18.0, 25.5, 30.2, 60.4, 76.7, 78.6, 93.9, 127.5, 127.6, 127.8, 127.9, 128.0, 128.2, 128.3, 128.6, 129.6, 132.9, 137.9, 138.1, 165.1; IR (NaCl/neat) 2942, 1200, 1177, 1110, 1023, 976, 868, 813, 700 cm$^{-1}$; HRMS (FAB+) calcd for C$_{26}$H$_{27}$O$_4$ (m/z) 403.1909, found (m/z) 403.1919.

(1R,2S)-1,2-Diphenyl-2-(tetrahydropyran 2-yloxy)ethanol (8S)

To 7S (2.11 g, 5.24 mmol) was added a solution of sodium hydroxide (295 mg, 7.38 mmol) in methanol (10.5 ml). After stirring for 18 h at rt, the reaction mixture was concentrated in vacuo. After addition of water, the product was extracted with dichloromethane twice and the organic layer was dried over anhydrous sodium sulfate. After concentration in vacuo, the residue was purified by silica gel chromatography (eluted with 8:1 hexane:AcOEt) to give 8S (1.25 g, 80%) as a white solid.

$[\alpha]^D_{25}$=+73.8 (CHCl$_3$, c=1); $^1$H NMR (major isomer: 400 MHz, CDCl$_3$) δ CHCl$_3$: 1.30–1.82 (m, 6H), 2.71 (bs, 1H), 3.18–3.44 (m, 2H), 4.47 (t, J=2.4Hz, 1H), 4.82 (d, J=5.8 Hz, 1H), 4.89 (d, J=5.8 Hz, 1H), 7.18–7.31 (m, 10H); $^{13}$C NMR (major isomer: 100 MHz, CDCl$_3$) δ CHCl$_3$: 19.1, 25.3, 30.6, 62.0, 77.2, 81.5, 95.7, 127.3, 127.4, 127.6, 127.7, 127.9, 128.0, 137.9, 140.6; IR (NaCl/neat) 2923, 2851, 1726, 1452, 1268, 1111, 1069, 1025, 710, 699 cm$^{-1}$; HRMS (FAB+) calcd for C$_{19}$H$_{23}$O$_3$ (m/z) 299.1647, found (m/z) 299.1643.

(1R,2S)-1-tert-Butoxycarbonylmethoxy-1,2-diphenyl-2-(tetrahydropyran-2-yloxy)ethane (9S)

To a suspension of sodium hydride (60% oil dispersion; 161 mg, 4.03 mmol) in dry tetrahydrofuran (9.6 ml) were added a solution of 8S (1.15 g, 3.84 mmol) and tert-butyl bromoacetate (681 μl, 4.61 mmol) in dry tetrahydrofuran (9.6 ml) at 0° C. After stirring for 18 h at rt, the reaction mixture was concentrated in vacuo. After addition of water, the product was extracted with ethyl acetate twice and the organic layer was dried over anhydrous sulfate. After concentration in vacuo, the residue was purified by silica gel chromatography (eluted with 10:1 hexane:AcOEt) to give 9S (1.17 g, 74%) as a white solid.

$[\alpha]^D_{25}$=+29.8 (CHCl3, c=1); $^1$H NMR (major isomer: 400 MHz, CDCl$_3$) δ CHCl$_3$: 1.21–1.65 (m, 6H), 1.32 (s, 9H), 3.04 (dt, J=2.8, 11.2 Hz, 1H), 3.18 (bd, J=11.2 Hz, 1H), 3.68 (d, J=15.8 Hz, 1H), 3.81 (d, J=15.8 Hz, 1H), 4.41 (t, J=2.4 Hz, 1H), 4.55 (d, J=6.4 Hz, 1H), 4.82 (d, J=6.4 Hz, 1H), 7.15–7.31 (m, 10H); $^{13}$C NMR (major isomer: 100 MHz, CDCl$_3$) δ CHCl$_3$: 18.2, 25.4, 28.0, 30.3, 60.4, 67.3, 79.3, 81.1, 85.3, 93.8, 127.4, 127.5, 127.7, 127.8, 128.3, 128.4, 138.7, 138.9, 169.2; IR (NaCl/neat) 2940, 1751, 1727, 1368, 1200, 1164, 1125, 1022, 985, 700 cm$^{-1}$; HRMS (FAB+) calcd for C$_{25}$H$_{33}$O$_5$ (m/z) 413.2328, found (m/z) 413.2314.

(5R,6S)-5,6-Diphenyl-[1,4]dioxin-2-one (2b)

To a solution of 9S (1.03 g, 2.49 mmol) in methanol (5.0 ml) was added p-toluenesulfonic acid monohydrate (95 mg, 0.50 mmol). After stirring for 40 min at rt, the reaction mixture was concentrated in vacuo. After addition of a saturated aqueous solution of sodium bicarbonate, the product (alcohol) was extracted with ethyl acetate three times and the organic layer was dried over anhydrous sodium sulfate. After concentration, the residue was dissolved in toluene (5 ml) followed by addition of trifluoroacetic acid (192 μl, 2.49 mmol). After stirring for 3 h at 85° C., to the reaction mixture was added a saturated aqueous solution of sodium bicarbonate. The product was extracted with ethyl acetate three times and the organic layer was dried over anhydrous sulfate. After concentration in vacuo, the residue was purified by silica gel chromatography (eluted with 8:1 hexane:AcOEt) to give 2b (363 mg, 57%, >95% e.e.) as a white solid. Enantiomeric purity was determined by normal phase HPLC using a Chiralpak AS column (eluted with 4:1 hexane:AcOEt, 1.0 ml/min, inj. volume 50 μl; retention time=31.5 min (for the enantiomer, retention time=25.5 min)).

[a]$^D$ 221.3 (CHCl$_3$, c=1); $^1$H NMR (400 MHz, CDCl$_3$) δ CHCl$_3$: 4.64 (d, J=17.8 Hz, 1H), 4.82 (d, J- 17.8 Hz, 1H), 5.22 (d, J=3.4 Hz, 1H), 5.60 (d, J=3.4 Hz, 1H), 6.83–6.87 (m, 2H), 6.92–6.96 (m, 2H), 7.13–7.24 (m, 6H); $^{13}$C NMR (100 MHz, CDCl$_3$) δ CHCl$_3$: 66.7, 77.2) 84.2, 126.2, 127.6, 127.8, 128.1, 128.3, 128.5, 133.8, 134.8, 166.7; IR (NaCl/neat) 1743, 1384, 1341, 1217, 1124, 1053, 1035, 1018, 733, 700 cm$^{-1}$ HRMS (FAB+) calcd for C$_{16}$H$_{15}$O$_3$ (m/z) 255.1021, found (m/z) 255.1028.

(3S,5S,6R)-3-(tert-Butoxycarbonyloxy)methyl-5,6-diphenyl-[1,4]dioxin-2-one (10)

To a solution of 2b (60 mg, 0.23 mmol) in dry tetrahydrofuran (1.2 ml) was added a 0.6 M solution of sodium bis(trimethylsilyl)amide in toluene (0.59 ml, 0.35 mmol) at −78° C. After stirring for 30 min at −78° C., a solution of tert-butyl bromoacetate (104 μl, 0.71 mmol) in dry tetrahydrofuran (1.2 ml) was added. After stirring for 2 h at −78° C., a saturated aqueous solution of ammonium chloride (5 ml) was added. The product was extracted with ethyl acetate three times and the organic layer was dried over anhydrous sulfate. After concentration in vacuo, the residue was purified by thin layer chromatography (eluted with 6:1 hexane: AcOEt) to give 10 (49 mg, 54%) as a white solid.

$^1$H NMR (400 MHz, CDCl$_3$) δ CHCl$_3$: 1.45 (s, 9H, 2.87 (dd, J=4.0, 16.5 Hz, 1H), 3.09 (dd, J=6.5, 16.5 Hz, 1H), 4.85 (dd, J=4.0, 6.5 Hz), 5.49 (d, J=3.2 Hz, 1H), 5.92 (d, J=3.2 Hz, 1H), 7.05–7.26 (m, 10H); $^{13}$C NMR (100 MHz, CDCl$_3$) δ CHCl$_3$: 28.0, 39.0, 70.4, 74.4, 126.6, 127.6, 128.1, 128.3, 128.3, 128.4, 134.2, 134.4, 169.1, 169.2; IR (NaCl/neat) 1756, 1713 1212, 1154, 1102, 1048, 1.019, 695cm$^{-1}$; HRMS (FAB+) calcd for C$_{22}$H$_{25}$O$_5$ (m/z) 369.1632, found (m/z) 369.1667.

Obviously, numerous modifications and variations of the present invention are possible in light of the above teachings. It is therefore to be understood that within the scope of the appended claims, the invention may be practiced otherwise than as specifically described herein.

REFERENCES (1) (a) Sinclair, P. J.; Zhai, D.; Reibenspies, J.; Williams, R. M. J. Am. Chem. Soc. 1986, 108, 1103. (b) Aoyagi, Y; Iijima, A. Williams, R. M. J. Org. Chem. 2001, 66, 8010. and references cited in.

(2) (a) Andrus, M. B.; Soma Sekhar, E. L.; Meredith, E. L.; Dailey, N. K. Org. Lett. 2000, 2, 3035. (b) Andrus, M. B.; Meredith, E. L.; Soma Sekhar, E. L. Org. Lett. 2001, 3, 259. (c) Andrus, M. B.; Meredith, E. L.; Simmons, E. L.; Soma Sekhar, E. L.; Hicken E. J. Org. Lett. 2002, 4, 3549.

(3) Matsumura, Y.; Maki, T.; Murakami, S.; Onomura, O. J. Am. Chem. Soc. 2003, 125, 2052.

What is claimed is:

1. A lactone represented by the formula 2a or 2b:

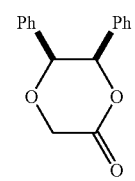

2a

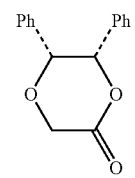

2b wherein each Ph is, independently, an unsubstituted phenyl group or a phenyl group substituted with one or more substituents selected from the group consisting of an alkoxy group, a nitro group, an alkyl group and a halogen.

2. The lactone of claim 1, which is represented by formula 2a.

3. The lactone of claim 1, which is represented by formula 2b.

4. The lactone of claim 1, wherein each Ph is an unsubstituted phenyl group.

5. The lactone of claim 1, which has at least 50% e.e.

6. The lactone of claim 1, which has at least 75% e.e.

7. The lactone of claim 1, which has at least 90% e.e.

8. The lactone of claim 1, which has at least 95% e.e.

9. A method of synthesizing the lactone of claim 1, comprising reacting a hydroxy ester of the formula:

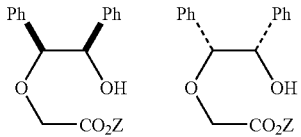

with an acid to produce the lactone, wherein Z is an alkyl group.

10. The method of claim 9, wherein the acid is hydrochloric acid, hydrobromic acid, hydroiodic acid, sulfuric acid, methanesulfonic acid, trifluoromethanesulfonic acid, benzenesulfonic acid, p-toluenesulfonic acid, trifluoroacetic acid ro acidic ion exchange resin (ion exchange resin acid catalyst).

11. The method of claim 9, wherein the acid is trifluoroacetic acid.

12. The method of claim 9, wherein Z is a tert-butyl group.

13. A method of synthesizing a substituted α-hydroxy acid represented by the formula:

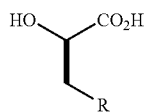

wherein R is a substituted alkyl group, an unsubstituted alkyl group, a substituted aryl group, an unsubstituted aryl group, a substituted alkoxycarbonyl group or an unsubstituted alkoxycarbonyl group, comprising:

treating the lactone of claim 1 with a base and a compound represented by the formula X—CH$_2$—R to produce a compound represented by the formula (12):

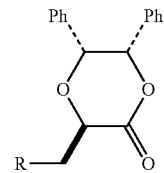

wherein X is a leaving group, followed by
catalytic hydrogenating the compound represented by the formula (12) to produce the substituted α-hydroxy acid.

14. The method of claim 13, wherein R is a tert-butoxycarbonyl group.

15. The method of claim 13, wherein X is Br—.

16. The method of claim 13, wherein R is a tert-butoxycarbonyl group and X is Br—.

17. The lactone of claim 1, wherein the alkoxy group has 1 to 7 carbon atoms.

18. The lactone of claim 1, wherein the alkyl group has 1 to 6 carbon atoms.

19. The lactone of claim 1, wherein the alkoxy group has 1 to 7 carbon atoms and the alkyl group has 1 to 6 carbon atoms.

20. The lactone of claim 1, wherein each Ph is, independently, a phenyl group substituted with one or more groups selected from the group consisting of an alkoxy group, a nitro group, an alkyl group and a halogen.

* * * * *